United States Patent [19]

Yonan

[11] 4,208,327
[45] Jun. 17, 1980

[54] 5-ARYL-1-(2-OXAZOLIN-2-YL)-1H-1,4-BENZODIAZEPINES AND RELATED COMPOUNDS

[75] Inventor: Peter K. Yonan, Morton Grove, Ill.

[73] Assignee: G. D. Searle & Co., Skokie, Ill.

[21] Appl. No.: 26,701

[22] Filed: Apr. 3, 1979

[51] Int. Cl.$^2$ ............... C07D 417/04; C07D 403/04; C07D 413/04
[52] U.S. Cl. ............... 260/239.3 R; 260/239 BD; 260/333; 260/243.3; 260/245.5; 260/245.6; 544/53; 544/96; 544/316; 544/331; 548/348; 424/244; 424/246; 424/251; 424/270; 424/272; 424/273 R; 424/275; 424/248.57; 424/248.54
[58] Field of Search ............... 260/239 BD, 239.3 R, 260/306.7 T, 307 A, 307 F, 333, 327 R; 544/316, 331, 96, 53; 548/348

[56] References Cited

U.S. PATENT DOCUMENTS

| 3,136,815 | 6/1964 | Reeder et al. | 260/562 |
| 3,371,085 | 2/1968 | Reeder et al. | 260/239.3 D |
| 3,481,921 | 12/1969 | Field et al. | 260/239 |

FOREIGN PATENT DOCUMENTS

| 749136 | 4/1970 | Belgium | 260/239.3 D |
| 785008 | 6/1972 | Belgium | 260/239.3 D |
| 1355170 | 6/1974 | United Kingdom | 260/239.3 D |

OTHER PUBLICATIONS

Sternbach, "Benzodiazpines", Raven Press (1973), pp. 1-26.

Lednicer et al., Organic Chemistry of Drum Synthesis, (1977), Chapter 18, "Benzodiazepines", pp. 363-371.
Szmuszkovicz et al., "Tetrahedron Letters", No. 39, pp. 3665-3668, (1971).

Primary Examiner—Henry R. Jiles
Assistant Examiner—Robert T. Bond
Attorney, Agent, or Firm—Dragan J. Karadzic

[57] ABSTRACT

5-Aryl-1-(2-oxazolin-2-yl)-1H-1,4-benzodiazepines and related compounds having the formula

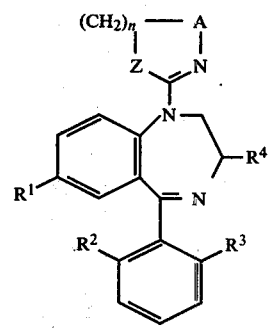

wherein A is methylene or carbonyl; Z is oxygen, imino or thio; $R^1$, $R^2$, and $R^3$ independently are hydrogen, halogen, trifluoromethyl or nitro; $R^4$ is hydrogen or hydroxy; and n is positive integer from 1 to 3 inclusive are disclosed. These compounds are useful because of their central nervous system activity.

17 Claims, No Drawings

5-ARYL-1-(2-OXAZOLIN-2-YL)-1H-1,4-BENZODIAZEPINES AND RELATED COMPOUNDS

The present invention relates to 5-aryl-1-(2-oxazolin-2-yl)-1H-1,4-benzodiazepines and related compounds having the following general formula

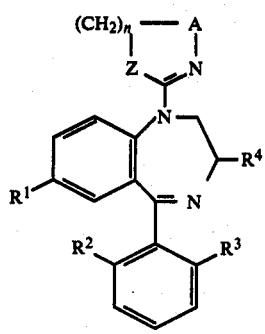

wherein A is methylene or carbonyl; Z is oxygen, imino or thio; $R^1$, $R^2$ and $R^3$ independently are hydrogen, halogen, trifluoromethyl or nitro; $R^4$ is hydrogen or hydroxy; and n is positive integer from 1 to 3 inclusive.

The halogens comprehended as substituents in the foregoing formula are chlorine, bromine, fluorine and iodine.

Embodiment of the present invention of the formula

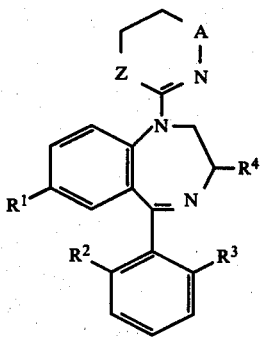

wherein A is methylene or carbonyl; Z is oxygen, imino or thio; $R^1$, $R^2$ and $R^3$ independently are hydrogen, halogen, trifluoromethyl or nitro; and $R^4$ is hydrogen or hydroxy are preferred.

Further preferred embodiments are compounds of the formula

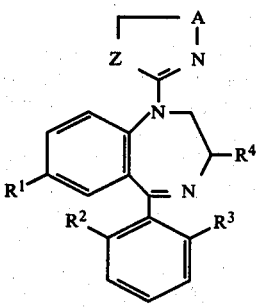

wherein A is methylene or carbonyl; Z is oxygen, imino or thio; $R^1$, $R^2$ and $R^3$ independently are hydrogen, halogen, trifluoromethyl or nitro; and $R^4$ is hydrogen or hydroxy.

Further preferred embodiments are compounds of the formula

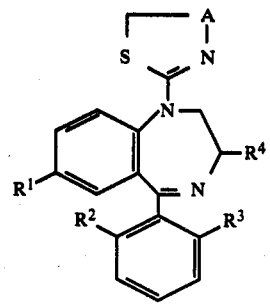

wherein A is methylene or carbonyl; $R^1$, $R^2$ and $R^3$ independently are hydrogen, halogen, trifluoromethyl or nitro; and $R^4$ is hydrogen or hydroxy.

Further preferred embodiments are compounds of the formula

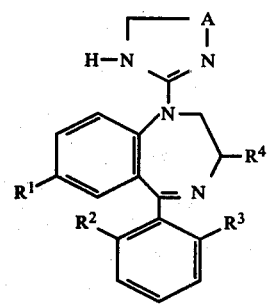

wherein A is methylene or carbonyl; $R^1$, $R^2$ and $R^3$ independently are hydrogen, halogen, trifluoromethyl or nitro; and $R^4$ is hydrogen or hydroxy.

Further preferred embodiments are compounds of the formula

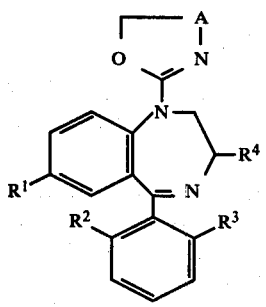

wherein A is methylene or carbonyl; $R^1$, $R^2$, and $R^3$ are independently hydrogen, halogen, trifluormethyl or nitro; and $R^4$ is hydrogen or hydroxy.

Further preferred embodiments are compounds of the formula

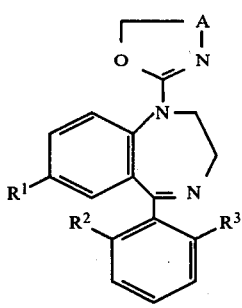

wherein A is methylene or carbonyl; and $R^1$, $R^2$ and $R^3$ independently are hydrogen or halogen.

Particularly preferred embodiments are compounds of the formula

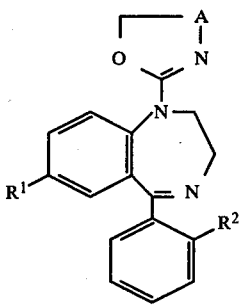

wherein A is methylene or carbonyl; and $R^1$ and $R^2$ independently are hydrogen or halogen.

The non-toxic pharmaceutically acceptable acid addition salts of the compounds of the present invention are also included within the scope of this invention. Both organic and inorganic acids can be employed to form such salts, illustrative acids being sulfuric, nitric, phosphoric, hydrochloric, hydrobromic, hydroiodic, citric, acetic, lactic, tartaric, sulfonic, succinnic, maleic, malic, cinnamic, benzoic, gluconic, ascorbic and related acids. These salts are readily prepared by methods known in the art.

The compounds of the present invention are useful because of their pharmacological properties. In particular, they are useful because of their central nervous system activity. The central nervous system activity of the present compounds is evident from their anticonvulsant, anti-anxiety, sedative-hypnotic and muscle relaxant properties. The duration of action of the present compounds is shown to be considerably shorter than that observed with other benzodiazepines.

The anti-convulsant activity of the present compounds is evident from their ability to block pentylenetetrazole induced clonic convulsions in mice [after Goodman, L. S. et al, J. Pharmac. Exp. Ther., 108, 168 (1953)]. In this experiment the duration of activity was determined for 7-chloro-5-(o-chlorophenyl)-2,3-dihydro-1-(2-oxazolin-2-yl)-1H-1,4-benzodiazepine (hereinafter referred to as Compound I), a representative compound of the present invention, and compared with that of diazepam, a standard benzodiazepine. Both test compounds were administered intragastrically at specific time periods prior to the pentylenetetrazole challenge, and the $ED_{50}$ for blockade of clonic convulsions was determined for each time period. Duration of activity is inferred from increases in the $ED_{50}$ with time.

Table 1 presents the $ED_{50}$'s for each of the tested time periods for Compound I and for diazepam.

Table 1

Anti-pentylenetetrazole effects in mice of intragastrically administered Compound I and diazepam. The $ED_{50}$'s (and the 95% confidence limits) in mg/kg units are presented for each time tested.

| Time | Compound I | Diazepam |
|---|---|---|
| 5 min | 3.8(2.9–5.1) | 1.1(.9–.14) |
| 15 min | 1.0(.8–1.2) | .9(.9–1.0) |
| 30 min | 1.9(1.5–2.3) | .8(.7–1.0) |
| 1 hour | 1.8(1.5–2.3) | .8(.6–1.1) |
| 2 hours | 6.2(5.0–7.7) | .7(.5–.8) |
| 4 hours | 7.1(5.8–8.8) | 1.6(1.3–2.0) |
| 8 hours | 19.6(15.7–24.6) | 1.4(1.0–1.9) |

Compound I reached its peak anti-pentylenetetrazole activity within 15 minutes of intragastic administration; the $ED_{50}$ nearly doubled in 30 minutes and increased about 20 fold by 8 hours. Diazepam also reached its peak activity within 15 minutes; the $ED_{50}$ remained stable for 2 hours and rose only 2 fold in 8 hours. This demonstrates that Compound I had a much shorter duration of activity than Diazepam.

Table 2 presents the $ED_{50}$'s for each of the tested time periods for intravenously administered Compound I and Diazepam.

Table 2

Anti-pentylenetetrazole effects in mice of intravenously administered Compound I and Diazepam. The $ED_{50}$'s (and the 95% confidence limits) in mg/kg are presented for each time period tested.

| Time | Compound | Diazepam |
|---|---|---|
| 1 min | .12(.09–.18) | .07(.05–.09) |
| 15 min | .18(.14–.24) | .26(.17–.38) |
| 30 min | .23(.16–.35) | .23(.16–.35) |
| 1 hour | .57(.41–.78) | .48(.38–.62) |
| 2 hours | 1.44(.93–2.22) | .75(.57–.97) |
| 4 hours | 4.79(3.22–7.13) | 1.16(.83–1.62) |
| 8 hours | 17.8(13.5–23.6) | 1.78(1.2–2.65) |

Compound I is effective as an anti-convulsant via intravenous route of administration as well as the intragastric route, and reaches peak activity within one minute. Also, whereas the $ED_{50}$'s for diazepam increased only 25 fold over the 8 hour period, the $ED_{50}$ for Compound I increased nearly 150 fold, demonstrating that Compound I has a shorter duration of activity via intravenous route as well as the intragastric route.

Anti-anxiety activity of the present compounds is evident from the anti-conflict results obtained in a multiple VI-FR conflict procedure in the squirrel monkey (after Cook, L. and Sepinwall, J., In: Mechanism of Action of Benzodiazepines, ed. by E. Costa and P. Grengard pp. 1–28, Raven Press, N.Y. 1957). In this procedure squirrel monkeys were trained to press a lever for intermittant food reinforcement. Seven 5 minute VI-60" periods alternated with six 2 minute FR-10 periods. Different cues accompanied both schedules. The FR-10 periods were the conflict periods since the animals received a brief electric shock to their feet along with the food pellet. The compound and vehicle control administrations were via intragastric route. The results for 7-chloro-5-(o-chlorophenyl)-2,3-dihydro-1-(2-oxazolin-2-yl)-1H-1,4-benzodiazepine (hereinafter referred to as Compound I), a representative compound of the present invention, are presented in Table 3.

Table 3

Effect of Compound I in the multiple V1-FR conflict procedure. For each dose tested the change in group bar pressing rates for both conflict and non-conflict segments are presented as percentages of average pre-compound control rates.

| Dose (mg/kg) | N | Conflict (FR) | Non-Conflict (VI) |
|---|---|---|---|
| .07 | 5 | 281 | 100 |
| .126 | 6 | 514 | 101 |
| .404 | 6 | 1286 | 100 |
| 1.26 | 5 | 1519 | 46 |

The compound bar pressing rates are presented in this table as percentages of the average pre-compound control rates. The table shows a clear dose responsive increase in bar pressing rates during the conflict segment demonstrating an anti-conflict effect. In an experiment investigating a comparison of durations of activity, a drug crossover design was employed with 14 squirrel monkeys. A molar equivalent dose of Compound I and diazepam was administered and the animals were tested 16 hours later. Whereas Compound I treatments produced near control bar pressings rates during the conflict segments (123% of pre-compound control levels) the diazepam treatments still produced pronounced anti-conflict effects (1265% of precompound control levels). This demonstrates the shorter duration of action of anti-anxiety effect of Compound I.

Sedative-hypnotic activity of the present compounds is evident from their ability to potentiate a sub-hypnotic dose of a barbiturate, pentobarbital sodium, in mice (after Rudzik, A.D. et al, In: *The Benzodiazepines*, ed. by S. Gazattini, E. Mussini and L. O. Randall, pp. 285-297, Raven Press, N.Y. 1973). In this procedure an $ED_{50}$ for loss of righting reflex was established. In order to determine the duration of action, pentobarbital sodium was administered at varying times after intragastric administration of 7-chloro-5-(o-chlorophenyl)-2,3-dihydro-1-(2-oxazolin-2-yl)-1H-1,4-benzodiazepine (hereinafter referred to as Compound I), a representative compound of the present invention, and $ED_{50}$'s for each time period were determined. Diazepam was also tested to provide a standard with which to compare durations of activity. Table 4 presents these results.

Table 4

Potentiation of a sub-hypnotic dose (20 mg/kg i.p.) of pentobarbital sodium as measured by loss of righting reflex in mice. $ED_{50}$'s (and 95% confidence limits) in mg/kg units are presented for each time period.

| Time (Hours) | Compound I | Diazepam |
|---|---|---|
| .25 | 5.6(3.8–8.4) | 4.1(2.7–6.3) |
| 1.0 | 24.1(17.9–32.4) | 3.8(2.7–5.4) |
| 2.0 | 39.1(28.1–54.3) | 3.6(2.4–5.4) |

The $ED_{50}$ for potentiating pentobarbital sodium for Compound I increased about 7 fold during the two hour period whereas the $ED_{50}$ for diazepam remained fairly stable. This demonstrates the shorter duration of sedative-hypnotic activity of Compound I as compared with a standard benzodiazepine.

Muscle relaxant properties of the present compounds are evident from the results of the rotarod test in mice. Using this procedure [after Dunham, N.W. and T.S. Miya, *J. Amer. Pharm. Assoc.*, 46 pp. 208-209 (1957)], 7-chloro-5-(o-chlorophenyl)-2,3-dihydro-1-(2-oxazolin-2-yl)-1H-1,4-benzodiazepine (hereinafter referred to as Compound I), a representative compound of the present invention, was compared with diazepam to determine a relative duration of activity. The compounds were administered intragastrically to mice at varying time periods before being placed on the horizontal rotating (4.4 rpm) rod. Different groups of mice were assigned to each time period so that a subject was tested only once. A testing trial consisted of two opportunities to stay on the rod for one minute. $ED_{50}$'s were calculated for each time period. The results are presented in Table 5.

Table 5

Rotarod effects: $ED_{50}$'s (and 95% confidence limits in mg/kg units are presented for each time period.

| Time (Hours) | Compound I | Diazepam |
|---|---|---|
| .08 | 8.5(6.6–10.8) | 6.0(4.29–8.35) |
| .25 | 2.9(1.7–5.0) | 3.2(2.3–4.4) |
| .5 | 8.9(6.4–12.3) | 5.0(3.6–6.9) |
| 1.0 | 24.0(17.3–33.3) | 5.7(3.4–9.5) |
| 2.0 | 74.9(57.1–98.3) | 7.7(5.49–10.9) |

Compound I produced its peak effect within 15 minutes and rapidly lost potency over the two hour period of testing; that is, the $ED_{50}$ increased 25 fold from 15 minutes to 2 hours. Diazepam also reached peak activity in 15 minutes but its $ED_{50}$ increased only about 2.5 times in the same time period. This demonstration that Compound I has a shorter duration of action.

Compounds of the present invention may be combined with common pharmaceutical carriers. These compositions can be administered either orally or parenterally. For oral administration tablets, lozenges, capsules, dragees, pills or powders are suitable, while aqueous solutions, nonaqueous solutions or suspensions are appropriate for parenteral administration. Acceptable pharmaceutical carriers are exemplified by gelatin capsules, sugars such as lactose or sucrose, starches such as corn starch or potatoe starch, cellulose derivatives such as sodium carboxymethyl cellulose, ethyl cellulose, methyl cellulose or cellulose acetate phthalate, gelatin, talc, calcium phosphate such as dicalcium phosphate or tricalcium phosphate, sodium sulfate, calcium sulfate, polyvinylpyrrolidone, acacia, polyvinyl alcohol, stearic acid, alkaline earth metal stearates such as magnesium sterate, vegtable oils such as peanut oil, cottonseed oil, sesame oil, olive oil, corn oil or theobroma, water, agar, alginic acid, benzyl alcohol, isotonic saline and phosphate buffer solutions as well as other non-toxic compatible substances.

The compounds of the present invention in which $R^4$ is hydrogen, A is methylene, Z is oxygen and $R^1$, $R^2$, $R^3$ and n are as previously defined are prepared by the method set out in Scheme I Scheme I

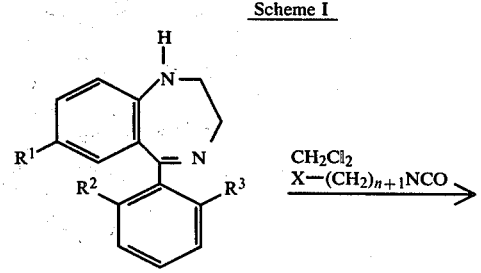

-continued
Scheme I

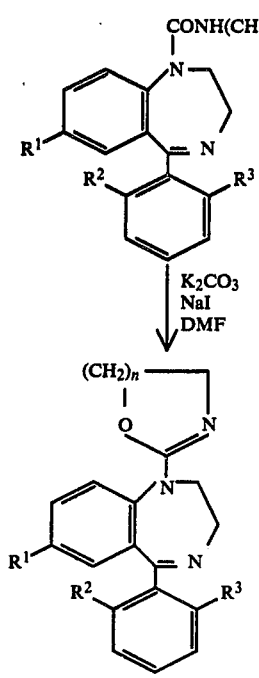

wherein X represents halogen, with chlorine and bromine being preferred.

The compounds of the present invention in which $R^4$ is hydrogen, A is methylene, Z is thio, and $R^1$, $R^2$, $R^3$ and n are as previously defined are prepared by the method set out in Scheme II.

Scheme II

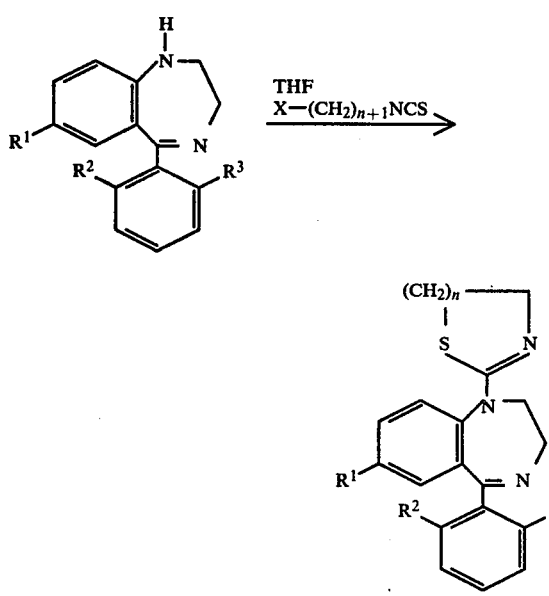

wherein X represents halogen, with chlorine and bromine being preferred.

The compounds of the present invention is which $R^4$ is hydrogen, A is carbonyl, Z is oxygen or thio, and $R^1$, $R^2$, $R^3$ and n are as previously defined are prepared by the method set out in Scheme III.

Scheme III

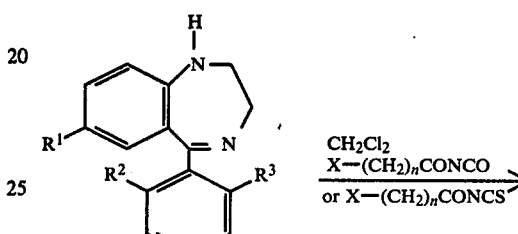

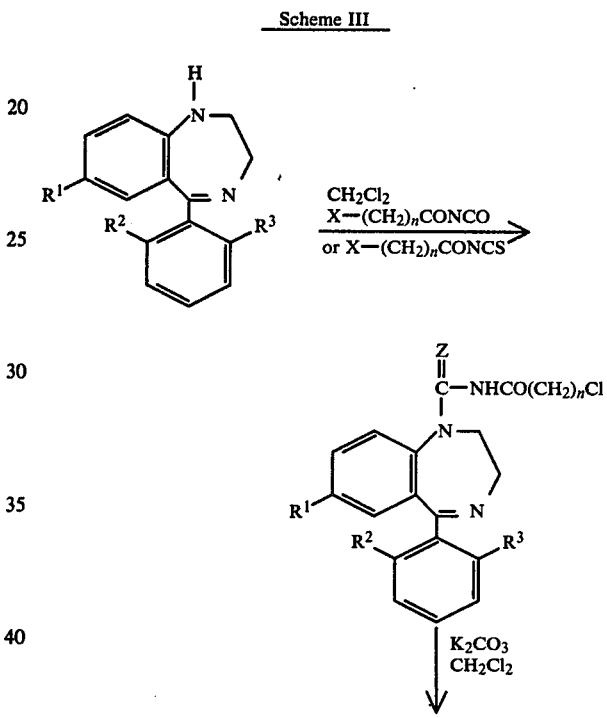

wherein X represents halogen, with chlorine and bromine being preferred.

The compounds of the present invention in which $R^4$ is hydrogen, A is methylene or carbonyl, Z is oxygen or thio, and $R^1$, $R^2$, $R^3$ and n are as previously defined are prepared by the method set out in Scheme IV.

Scheme IV
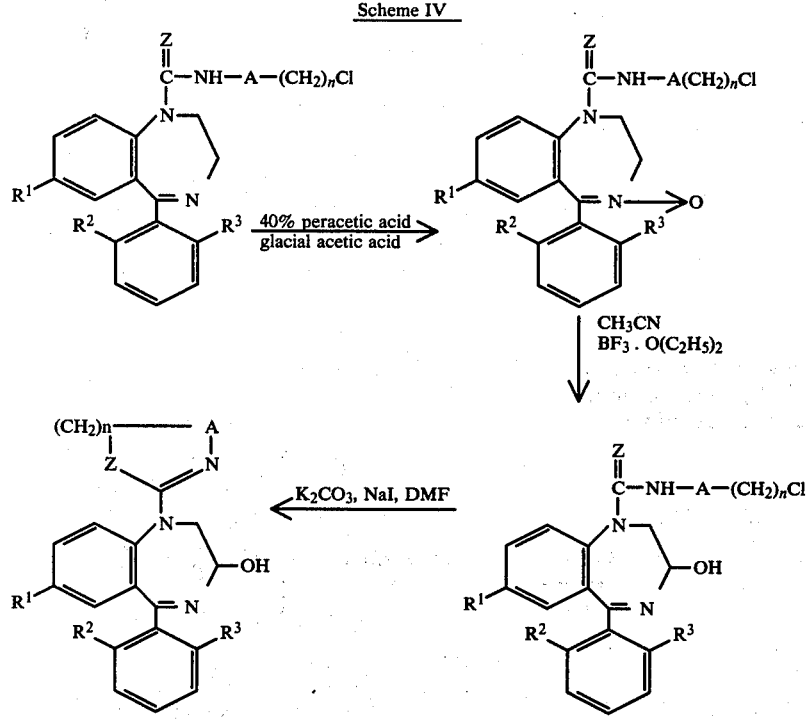
The compounds of the present invention in which A is methylene, Z is imino, and $R^1$, $R^2$, $R^3$, $R^4$ and n are as previously defined are prepared by the method set out in Scheme V.
Scheme V
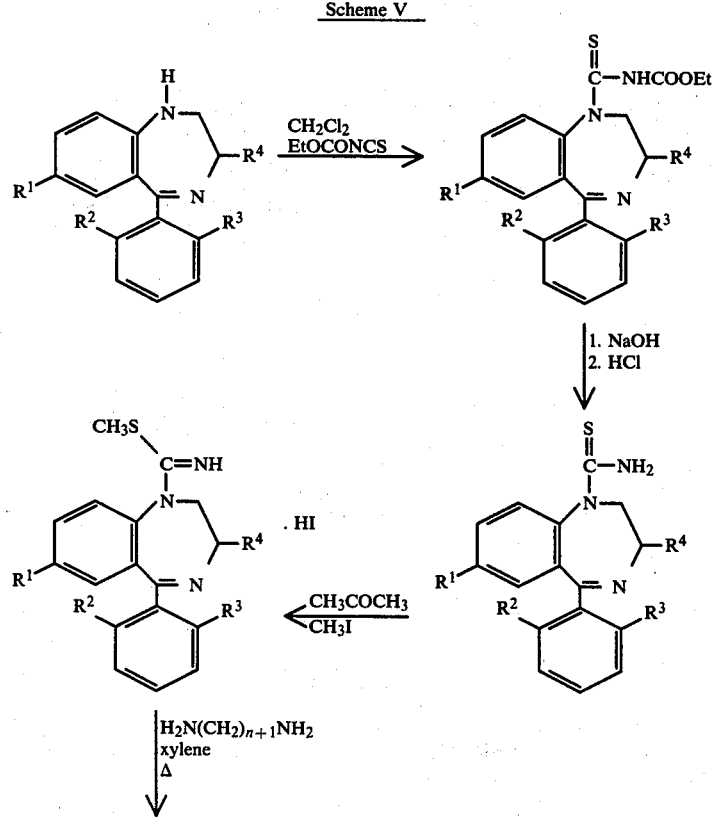

Scheme V

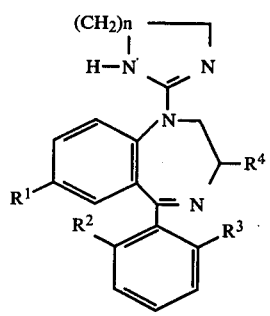

The compounds of the present invention in which A is carbonyl, Z is imino, and $R^1$, $R^2$, $R^3$, $R^4$ and n are as previously defined are prepared by the method set out in Scheme VI.

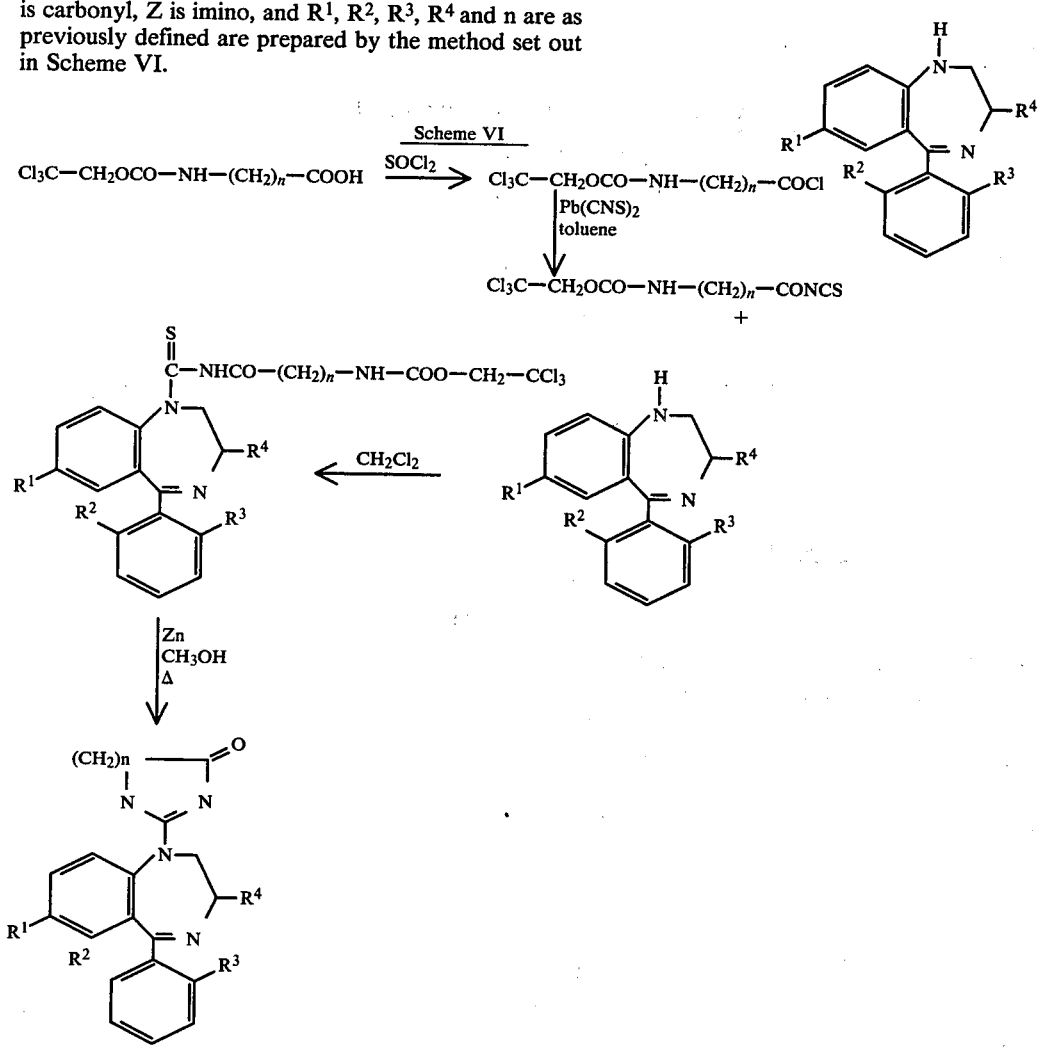

1H-1,4-Benzodiazepine starting materials of the formula wherein $R^1$, $R^2$, $R^3$, and $R^4$ are as previously defined; are known compounds or they can conveniently be prepared by known methods.

The invention will appear more fully from the examples which follow. The examples are not to be construed as limiting the invention either in spirit or in scope as variations both in materials and methods will be apparent to those skilled in the art. Throughout the examples hereinafter set forth, temperatures are given in degrees Centigrade (°C.) and quantity of materials in parts by weight unless parts by volume is specified. The relationship between parts by weight and parts by volume is the same as that existing between grams and milliliters.

EXAMPLE 1

A. 10 parts of 7-chloro-2,3-dihydro-5-phenyl-1H-1,4-benzodiazepine is dissolved in 75 parts by volume of methylene chloride. To this solution is added 6 parts of 2-chloroethylisocyanate and the resultant mixture left standing at ambient temperature for about 48 hours. Then, additional 2 parts of 2-chloroethylisocyanate is added to the mixture, the mixture heated on a steam bath for about 4 hours and the solvent removed to give a solid. The solid is washed with ether and crystallized from a mixture of methylene chloride and hexane to give 7-chloro-N-(2-chloroethyl)-2,3-dihydro-5-phenyl-1H-1,4-benzodiazepine-1-carboxamide, as yellow crystals melting at about 160°–161° C. This compound is represented by the following formula

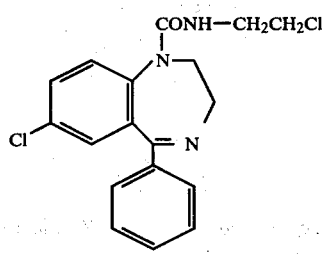

B. 10 parts of the above carboxamide, 12 parts of potassium carbonate, and 2 parts of sodium iodide are dissolved in 175 parts by volume of N,N-dimethylformamide. The resultant solution is stirred at about 90°–100° C. for about 4 hours, cooled and, then, poured into 1000 parts by volume of water. The precipitate which forms is extracted with methylene chloride, the methylene chloride layer dried and then the solvent removed. The residue is crystallized from a mixture of methylene chloride and hexane to give 7-chloro-2,3-dihydro-1-(2-oxazolin-2-yl)-5-phenyl-1H-1,4-benzodiazepine, melting at about 125°–126° C. This compound is represented by the following formula

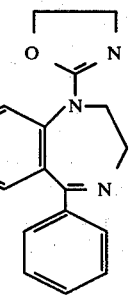

EXAMPLE 2

A. 25 Parts of 7-chloro-5-(o-chlorophenyl)-2,3-dihydro-1H-1,4-benzodiazepine is dissolved in 250 parts by volume of methylene chloride. To this solution 15 parts of 2-chloroethylisocyanate is slowly added with stirring. The resultant mixture is stirred at ambient temperature for about 90 minutes. The resulting dark brown solution is filtered through a layer of activated magnesium silicate, the filtrate dried and treated with charcoal. After removal of charcoal by filtration the solvent is removed from the resultant filtrate to affort an oil. This oil is dissolved in about 100 parts by volume of ether and the resultant solution cooled to give 7-chloro-N-(2-chloroethyl)-5-(o-chlorophenyl)-2,3-dihydro-1H-1,4-benzodiazepine-1-carboxamide as crystalline solid melting at about 150°–153° C. This compound is represented by the following formula

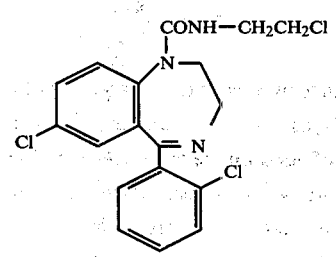

B. 21.5 Parts of the above carboxamide, 25 parts of potassium carbonate, and 2.5 parts of sodium iodide are dissolved in 350 parts by volume of acetonitrile and the resultant reaction mixture stirred at reflux temperature for about six hours. The salts which form are filtered off and washed with acetonitrile. The filtrate is stripped and the residue extracted with methylene chloride. The methylene chloride layer is dried and treated with charcoal. After removal of charcoal by filtration the solvent is removed from the filtrate to give an oil which, upon crystallization form a mixture of ether and hexane, affords 7-chloro-5-(o-chlorophenyl)-2,3-dihydro-1-(2-oxazolin-2-yl)-1H-1,4-benzodiazepine, as a crystalline solid melting at about 110°–111° C. This compound is represented by the following formula

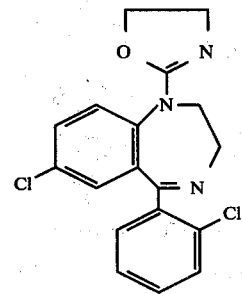

EXAMPLE 3

The mixture of 8 parts of 7-chloro-5-(o-chlorophenyl)-2,3-dihydro-1H-1,4-benzodiazepine, 4.9 parts of chloroacetylisocyanate, and 200 parts by volume of methylene chloride is stirred under nitrogen atmosphere at ambient temperature for about one hour. The mixture is then filtered through a layer of activated magnesium silicate and the filtrate evaporated to dryness. The resultant yellow oil is dissolved in ether and the solvent removed by evaporation to give gummy residue which upon crystallization from ether affords 7-chloro-N-chloracetyl-5-(o-chlorophenyl)-2,3-dihydro-1H-1,4-benzodiazepine-1-carboxamide, as a yellow solid melting at about 152°-156° C. This compound is represented by the following formula

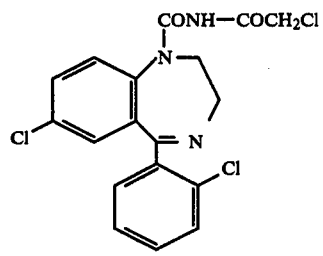

The mixture of 5 parts of the above carboxamide, 7.3 parts of anhydrous potassium carbonate and 200 parts by volume of acetonitrile is stirred at ambient temperature for about 24 hours, then filtered and evaporated to dryness. The residue is dissolved in a mixture of methylene chloride and water, the layers separated, and the methylene chloride fraction dried over magnesium sulfate and evaporated to give sticky yellow solid. The crude solid after trituration with ether affords 7-chloro-5-(o-chlorophenyl)-2,3-dihydro-1-(4-oxo-2-oxazolin-2-yl)-1H-1,4-benzodiazepine, as a light yellow solid melting at about 224°-228° C. This compound is represented by the following formula

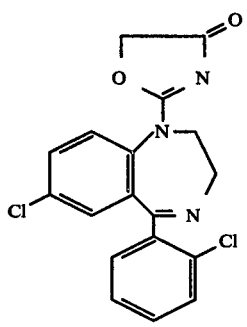

EXAMPLE 4

Substitution of an equivalent quantity of 7-fluoro-5-(o-fluorophenyl)-2,3-dihydro-1H-1,4-benzodiazepine for 7-chloro-5-(o-chlorophenyl)-2,3-dihydro-1H-1,4-benzodiazepine called for in the procedure of Example 2A, affords N-(2-chloroethyl)-7-fluoro-5-(o-fluorophenyl)-2,3-dihydro-1H-1,4-benzodiazepine-1-carboxamide, melting at about 160°-162° C. after crystallization from ether. This compound is represented by the following formula

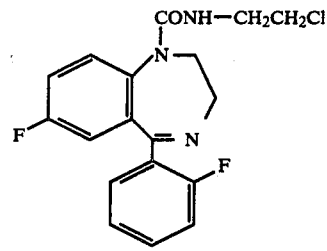

Substitution of an equivalent quantity of the above carboxamide in the procedure of Example 2B, affords 7-fluoro-5-(o-fluorophenyl)-2,3-dihydro-1-(2-oxazolin-2-yl)-1H-1,4-benzodiazepine, melting at about 180°-181° C. after crystallization from a mixture of methylene chloride and hexane. This compound is represented by the following formula

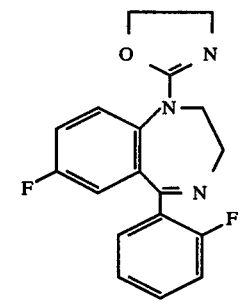

EXAMPLE 5

When an equivalent quantity of 7-chloro-5-(o-fluorophenyl)-2,3-dihydro-1H-1,4-benzodiazepine is substituted in the procedure of Example 2A there is obtained 7-chloro-N-(2-chloroethyl)-5-(o-fluorophenyl)-2,3-dihydro-1H-1,4-benzodiazepine-1-carboxamide, melting at about 138°-140° C. after crystallization from ether. This compound is represented by the following formula

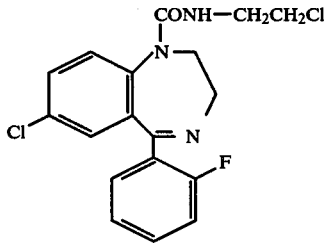

Substitution of an equivalent quantity of the preceeding carboxamide in the procedure of Example 2B affords 7-chloro-5-(o-fluorophenyl)-2,3-dihydro-1-(2-oxazolin-2-yl)-1H-1,4-benzodiazepine, melting at about 162°-164° C. after crystallization from a mixture of methylene chloride and hexane. This compound is represented by the following formula

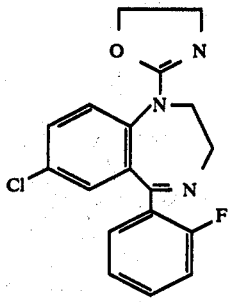

EXAMPLE 6

The solution of 8 parts of 7-chloro-5-(o-chlorophenyl)-2,3-dihydro-1H-1,4-benzodiazepine and 12.5 parts of 2-chloroethylisothiocyante in 110 parts by volume of tetrahydrofuran is stirred at reflux temperature for about 64 hours. The reaction mixture is then cooled to ambient temperature, filtered and the filtrate evaporated to dryness. The solid residue is washed with ether and crystallized from a mixture of methylene chloride and hexane to give 7-chloro-5-(o-chlorophenyl)-2,3-dihydro-1-(2-thiazolin-2-yl)-1H-1,4-benzodiazepine, melting at about 123°–124° C. This compound is represented by the following formula

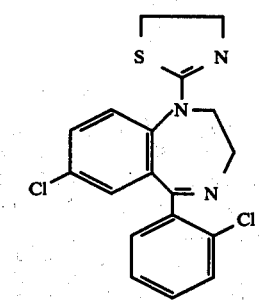

EXAMPLE 7

4 Parts of 7-chloro-5-(o-chlorophenyl)-2,3-dihydro-1H-1,4-benzodiazepine is dissolved in 50 parts by volume of methylene chloride and then 5 parts of chloroacetylisothiocyanate added to the solution. The reaction mixture is stirred at ambient temperature for about 17 hours, filtered and the filtrate evaporated to give, as crude oil, 7-chloro-N-chloroacetyl-5-(o-chlorophenyl)-2,3-dihydro-1H-1,4-benzodiazepine-1-carbothioamide. This compound is represented by the following formula.

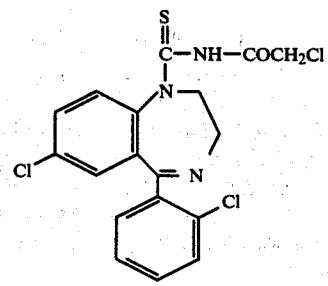

The above crude oil is refluxed with 4 parts of potassium carbonate in 100 parts by volume of acetonitrile for about 2.5 hours. The resultant reaction mixture is filtered through a layer of activated magnesium silicate to remove dark coloration and the filtrate evaporated. The residue is dissolved in methylene chloride, washed with water, dried over magnesium sulfate and concentrated by evaporation. Addition of hexane to the concentrated residue affords, as crystalline solid, 7-chloro-5-(o-chlorophenyl)-2,3-dihydro-1-(4-oxo-2-thiazolin-2-yl)-1H-1,4-benzodiazepine melting at about 217°–218° C. This compound is represented by the following formula

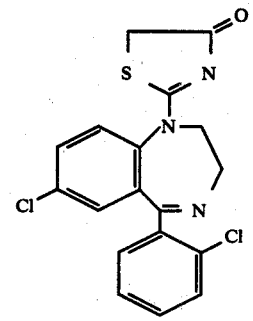

EXAMPLE 8

A mixture of 6 parts of 2,3-dihydro-7-nitro-5-phenyl-1H-1,4-benzodiazepine, 10 parts of 2-chloroethylisocyanate, 18 parts of potassium carbonate, 2 parts of sodium iodide and 150 parts by volume of acetonitrile is stirred at reflux temperature for about 50 hours, filtered and then the solvent removed by evaporation. The residue is dissolved in methylene chloride, washed with water, dried over magnesium sulfate and, then, the solvent removed to give an oil. The oil is triturated in hexane to afford a solid which is a mixture of 2,3-dihydro-7-nitro-1-(2-oxazolin-2-yl)-5-phenyl-1H-1,4-benzodiazepine and N-(2-chloroethyl)-2,3-dihydro-7-nitro-5-phenyl-1H-1,4-benzodiazepine-1-carboxamide. This mixture is separated by chromatography on alumina using 5% methanol in methylene chloride as the eluant. The oxazoline fractions are combined and the solvent removed to give an oil which on trituration in hexane solidifies. This solid is 2,3-dihydro-7-nitro-1-(2-oxazolin-2-yl)-5-phenyl-1H-1,4-benzodiazepine and is represented by the following formula

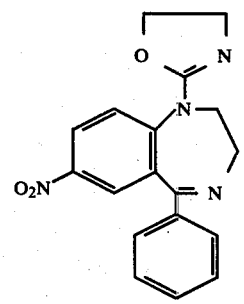

EXAMPLE 9

5 Parts of 7-chloro-5-(o-chlorophenyl)-2,3-dihydro-1H-1,4-benzodiazepine and 12 parts of 3-chloropropionylisothiocyanate is dissolved in 100 parts by volume of tetrahydrofuran and the resultant solution refluxed for about 18 hours. The reaction mixture is then cooled to ambient temperature and filtered. The solvent is removed from the filtrate and the residue crystallized from a mixture of methylene chloride and hexane to afford 7-chloro-5-(o-chlorophenyl)-2,3-dihydro-1-(5,6-dihydro-4-oxo-4H-1,3-thiazin-2-yl)-1H-1,4-benzodiazepine. This compound is represented by the following formula

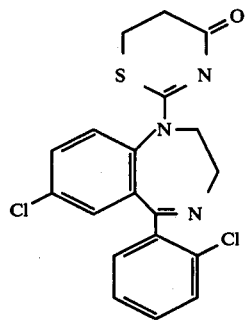

EXAMPLE 10

When an equivalent quantity of 3-chloropropylisoyanate is substituted in the procedure of Example 2A there is obtained 7-chloro-5-(o-chlorophenyl)-N-(3-chloropropyl)-2,3-dihydro-1H-1,4-benzodiazepine-1-carboxamide represented by the following formula

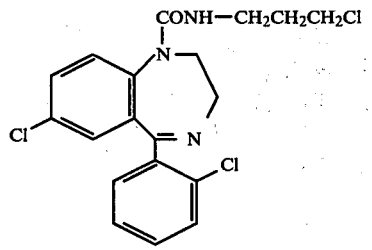

Substitution of an equivalent quantity of the preceeding carboxamide in the procedure of Example 2B affords 7-chloro-5-(o-chlorophenyl)-2,3-dihydro-1-(5,6-dihydro-4H-1,3-oxazin-2-yl)-1H-1,4-benzodiazepine represented by the following formula

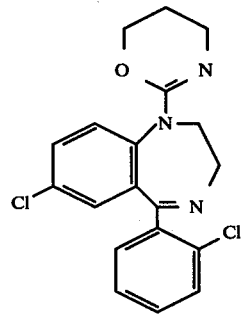

EXAMPLE 11

When an equivalent quantity of 3-chloropropylisothiocyanate is substituted in the procedure of Example 6 there is obtained 7-chloro-5-(o-chlorophenyl)-2,3-dihydro-1-(5,6-dihydro-4H-1,3-thiazin-2-yl)-1H-1,4-benzodiazepine represented by the following formula

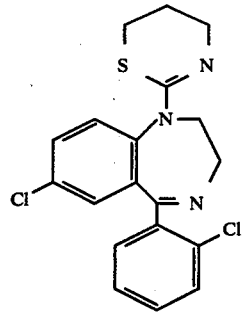

EXAMPLE 12

When an equivalent quantity of 3-bromopropionylisocyanate is substituted in the procedure of Example 3, first paragraph, there is obtained 7-chloro-5-(o-bromopropionyl)-2,3-dihydro-1H-1,4-benzodiazepine-1-carboxamide represented by the following formula

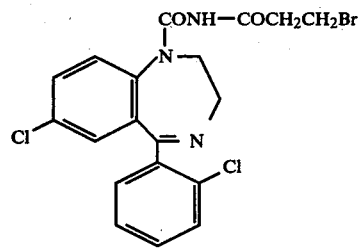

Substitution of the preceeding carboxamide in the procedure of Example 3, second paragraph, affords 7-chloro-5-(o-chlorophenyl)-2,3-dihydro-1-(5,6-dihydro-4-oxo-4H-1,3-oxazin-2-yl)-1H-1,4-benzodiazepine melting at about 124°–135° C. after crystallization from a mixture of hexane and ether. This compound is represented by the following formula.

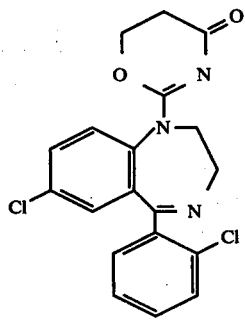

EXAMPLE 13

10 Parts of 7-chloro-N-(2-chloroethyl)-5-(o-chlorophenyl)-2,3-dihydro-1H-1,4-benzodiazepine-1-carboxamide is dissolved in 50 parts by volume of glacial acetic acid and to this solution 10 parts by volume of 40% peracetic acid is added all at once with stirring. The reaction mixture is stirred at ambient temperature for about 24 hours and then slowly poured into 1000 parts by volume of cold water. The precipitate which forms is extracted with methylene chloride, the extract dried over magnesium sulfate and the solvent removed. The residue crystallizes from ethanol to afford 7-chloro-N-(2-chloroethyl)-5-(o-chlorophenyl)-2,3-dihydro-1H-1,4-benzodiazepine-1-carboxamide 4-oxide. This compound is represented by the following formula

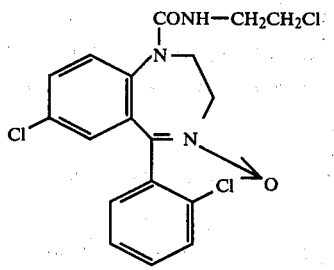

To a solution of 10 parts of the preceding carboxamide 4-oxide in 100 parts by volume of acetonitrile is added dropwise with stirring at ambient temperature 10 parts of trifluoroborane monoetherate. The reaction mixture is stirred overnight at ambient temperature, poured into cold water and extracted with methylene chloride. The methylene chloride extract is dried over magnesium sulfate, evaporated to a low volume and crystallized by the addition of hexane to afford 7-chloro-N-(2-chloroethyl)-5-(o-chlorophenyl)-2,3-dihydro-3-hydroxy-1H-1,4-benzodiazepine-1-carboxamide. This compound is represented by the following formula

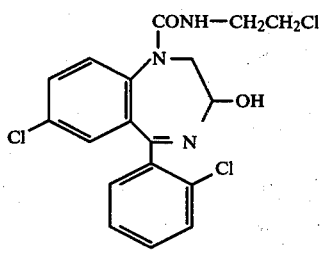

Substitution of an equivalent quantity of the above hydroxycarboxamide in the procedure of Example 2B affords 7-chloro-5-(o-chlorophenyl)-2,3-dihydro-3-hydroxy-1-(2-oxazolin--yl)-1H-1,4-benzodizepine. This compound is represented by the following formula

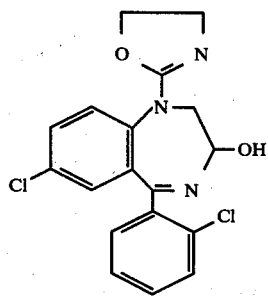

EXAMPLE 14

10 Parts of 7-chloro-5-(o-chlorophenyl)-2,3-dihydro-1H-1,4-benzodiazepine is dissolved in 100 parts by volume of methylene chloride and to this solution is added 5 parts of ethoxycarbonylisothiocyanate dropwise with stirring. The resulting reaction solution is then concentrated, hexane added to form precipitate and the precipitate saponified by the addition of ethanol solution of dilute sodium hydroxide. The resultant basic solution is neutralized by the addition of dilute hydrochloric acid to pH=7. The precipitate which forms is washed with water and dried to afford, 7-chloro-5-(o-chlorophenyl)-2,3-dihydro-1H-1,4-benzodiazepine-1-carbothioamide as a solid. This compound is represented by the following formula

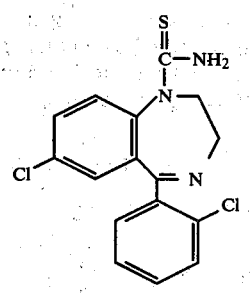

5 Parts of the preceeding carbothioamide is dissolved in 50 parts by volume of acetone and then 5 parts of methyl iodide is added to the solution. The solution is stirred overnight at about 50° C. then ether is added to the solution to precipitate 7-chloro-5-(o-chlorophenyl)-2,3-dihydro-α-methylthio-1H-1,4-benzodiazepine-1-methanimine hydroiodide. This compound is represented by the following formula

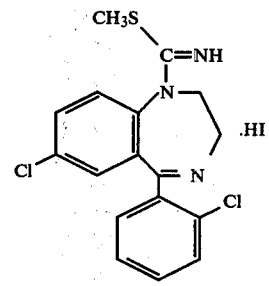

A solution of 7 parts of the above methanimine hydroiodide, and 10 parts of 1,2-ethanediamine in xylene is stirred at reflux temperature for about 5 hours. Then the reaction solution is cooled to ambient temperature, filtered and the solvent removed. The residue is crystallized from a mixture of methylene chloride and hexane to afford 7-chloro-5-(o-chlorophenyl)-2,3-dihydro-1-(2-imidazolin-2-yl)-1H-1,4-benzodiazepine. This compound is represented by the following structural formula

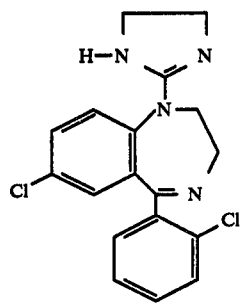

EXAMPLE 15

When an equivalent quantity of 4-chlorobutyrylisocyanate is substituted in the procedure of Example 3, first paragraph, there is obtained 7-chloro-N-(4-chlorobutyryl)-5-(o-chlorophenyl)-2,3-dihydro-1H-1,4-benzodiazepine-1-carboxamide represented by the following formula

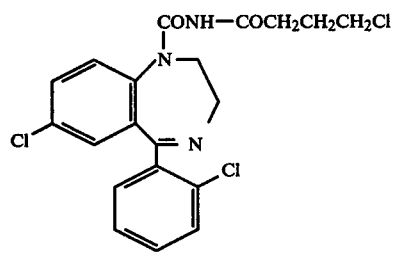

Substitution of the preceeding carboxamide in the procedure of Example 3, second paragraph, affords 7-chloro-5-(o-chlorophenyl)-2,3-dihydro-1-(4-oxo-4,5,6,7-tetrahydro-1,3-oxazepin-2-yl)-1H-1,4-benzodiazepine as a crystalline solid melting at about 187°–189.5° C. after crystallization from ether. This compound is represented by the following formula

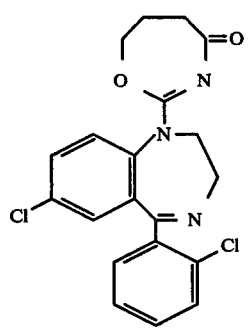

EXAMPLE 16

To a solution of 25 parts of N-[(2,2,2-trichloroethoxy)carbonyl]glycine in 250 parts by volume of toluene is added dropwise with stirring 20 parts of thionyl chloride. The resultant reaction mixture is heated on a steam bath for about 2 hours, then the solvent and excess of thionyl chloride are removed by distillation to afford {[(2,2,2-trichloroethoxy)carbonyl]amino} acetyl chloride represented by the following formula

Cl₃C—CH₂—O—CO—NHCH₂CO—Cl

A solution of 20 parts of the preceeding acetyl chloride and 30 parts of lead thiocyanate in 150 parts by volume of toluene is refluxed for about 4 hours, then cooled to ambient temperature and filtered. The solvent is removed from the filtrate and the remaining oil distilled using fractionating column under vacuum to give {[(2,2,2-trichloroethoxy)carbonyl]amino}acetyl isothiocyanate. This compound is represented by the following formula

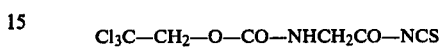

Cl₃C—CH₂—O—CO—NHCH₂CO—NCS

When an equivalent quantity of the preceeding acetyl isothiocyanate is substituted in the procedure of Example 3, first paragraph, there is obtained 7-chloro-5-(o-chlorophenyl)-2,3-dihydro-N-{[[(2,2,2-trichloroethoxy)-carbonyl]amino]acetyl}-1H-1,4-benzodiazepine-1-carbothioamide. This compound is represented by the following formula

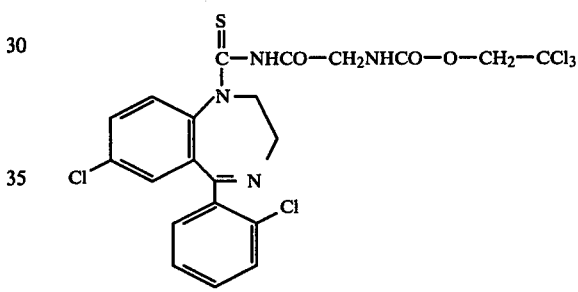

A solution of 10 parts of the above carboxamide and 5 parts of zinc dust in 150 parts by volume of methanol is refluxed for about 3 hours, then filtered and the solvent removed from the filtrate. The residue is crystallized from a mixture of methylene chloride and hexane to afford 7-chloro-5-(o-chlorophenyl)-2,3-dihydro-1-(4-oxo-2-imidazolin-2-yl)-1H-1,4-benzodiazepine. This compound is represented by the following formula

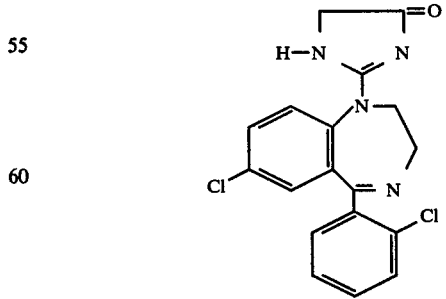

What is claimed is:

1. A compound of the formula

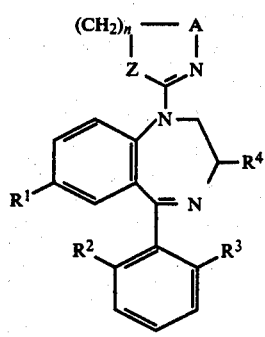

wherein A is methylene or carbonyl; Z is oxygen, imino or thio; $R^1$, $R^2$ and $R^3$ independently are hydrogen, halogen, trifluoromethyl or nitro; $R^4$ is hydrogen or hydroxy; and n is positive integer from 1 to 3 inclusive.

2. A compound according to claim 1 having the formula

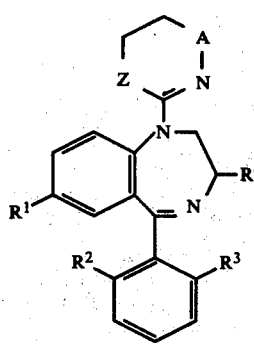

wherein A is methylene or carbonyl; Z is oxygen; imino or thio; $R^1$, $R^2$ and $R^3$ independently are hydrogen, halogen trifluoromethyl or nitro; and $R^4$ is hydrogen or hydroxy.

3. A compound according to claim 1 having the formula

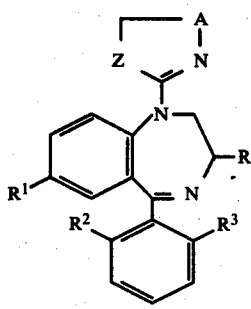

wherein A is methylene or carbonyl; Z is oxygen, imino or thio; $R^1$, $R^2$ and $R^3$ independently are hydrogen, halogen, trifluromethyl or nitro; and $R^4$ is hydrogen or hydroxy.

4. A compound according to claim 1 having the formula

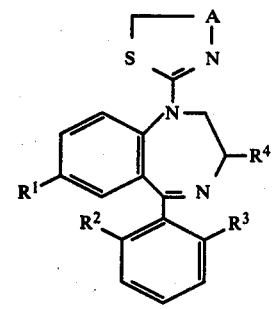

wherein A is methylene or carbonyl; $R^1$, $R^2$ and $R^3$ independently are hydrogen, halogen, trifluoromethyl or nitro; and $R^4$ is hydrogen or hydroxy.

5. A compound according to claim 1 having the formula

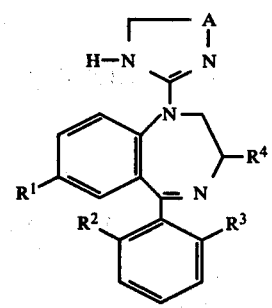

wherein A is methylene or carbonyl; $R^1$, $R^2$ and $R^3$ independently are hydrogen, halogen, trifluoromethyl or nitro; and $R^4$ is hydrogen or hydroxy.

6. A compound according to claim 1 having the formula

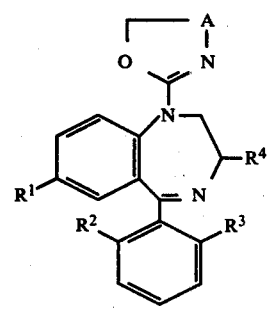

wherein A is methylene or carbonyl; $R^1$, $R^2$ and $R^3$ are independently hydrogen, halogen, trifluoromethyl or nitro; and $R^4$ is hydrogen or hydroxy.

7. A compound according to claim 1 having the formula

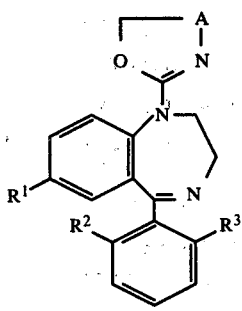

wherein A is methylene or carbonyl; and R¹, R² and R³ independently are hydrogen or halogen.

8. A compound according to claim 1 having the formula

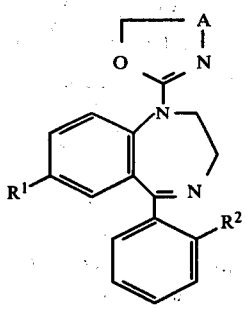

wherein A is methylene or carbonyl; and R¹, R² independently are hydrogen or halogen.

9. A compound according to claim 1 which is 7-chloro-2,3-dihydro-1-(2-oxazolin-2-yl)-5-phenyl-1H-1,4-benzodiazepine.

10. A compound according to claim 1 which is 7-chloro-5-(o-chlorophenyl)-2,3-dihydro-1-(2-oxazolin-2-yl)-1H-1,4-benzodiazepine.

11. A compound according to claim 1 which is 7-fluoro-5-(o-fluorophenyl)-2,3-dihydro-1-(2-oxazolin-2-yl)-1H-1,4 benzodiazepine.

12. A compound according to claim 1 which is 7-chloro-5-(o-fluorophenyl)-2,3-dihydro-1-(2-oxazolin-2-yl)-1H-1,4-benzodiazepine.

13. A compound according to claim 1 which is 7-chloro-5-(o-chlorophenyl)-2,3-dihydro-1-(4-oxo-2-oxazolin-2-yl)-1H-1,4-benzodiazepine.

14. A compound according to claim 1 which is 7-chloro-5-(o-chlorophenyl)-2,3-dihydro-1-(2-thiazolin-2-yl)-1H-1,4-benzodiazepine.

15. A compound according to claim 1 which is 7-chloro-5-(o-chlorophenyl)-2,3-dihydro-1-(4-oxo-2-thiazolin-2-yl)-1H-1,4-benzodiazepine.

16. A compound according to claim 1 which is 7-chloro-5-(o-chlorophenyl)-2,3-dihydro-1-(4-oxo-4,5,6,7-tetrahydro-1,3-oxazepin-2-yl)-1H-1,4-benzodiazepine.

17. A compound according to claim 1 which is 7-chloro-5-(o-chlorophenyl)-2,3-dihydro-1-(5,6-dihydro-4-oxo-4H-1,3-oxazin-2-yl)-1H-1,4-benzodiazepine.

* * * * *